United States Patent [19]
Müllner et al.

[11] Patent Number: 5,976,811
[45] Date of Patent: Nov. 2, 1999

[54] ANTIBODIES FOR THE SELECTIVE IMMUNOLOGICAL DETERMINATION OF BILE ACIDS IN BIOLOGICAL MATRICES

[75] Inventors: Stefan Müllner, Hochheim; Axel Hoffmann, Frankfurt, both of Germany

[73] Assignee: Hoescht Aktiengesellschaft, Frankfurt am Main, Germany

[21] Appl. No.: 08/807,457

[22] Filed: Feb. 28, 1997

[30] Foreign Application Priority Data

Mar. 6, 1996 [DE] Germany .......................... 196 08 592

[51] Int. Cl.$^6$ .......................... G01N 33/53; C07K 16/18; A61K 39/395
[52] U.S. Cl. .................................. 435/7.1; 435/4; 435/7.9; 435/7.95; 435/975; 530/387.1; 530/388.9; 530/389.8; 530/389.2; 530/388.24
[58] Field of Search ............................... 530/387.1, 388.9, 530/389.8, 388.24, 389.2; 435/4, 7.5, 7.9–7.95, 975

[56] References Cited

PUBLICATIONS

CA 125:81283, May, 1996.
CA 121:174671, Jun. 1994.
K.D.R. Setchell and A. Matsui, *Clinica Chemica Acta*, 127 (1983) pp. 1–17.
A. Roda et al., *Talanta*, vol. 31, No. 10B, pp. 895–900, 1984.

*Primary Examiner*—Julie Burke
*Attorney, Agent, or Firm*—Finnegan, Henderson, Farabow, Garrett & Dunner, L.L.P.

[57] ABSTRACT

Antibodies for the selective immunological determination of bile acids in biological matrices Polyclonal antibodies for the selective immunological determination of bile acids in biological matrices, a process for the preparation of these antibodies, and their use in immunoassays are described.

10 Claims, 1 Drawing Sheet

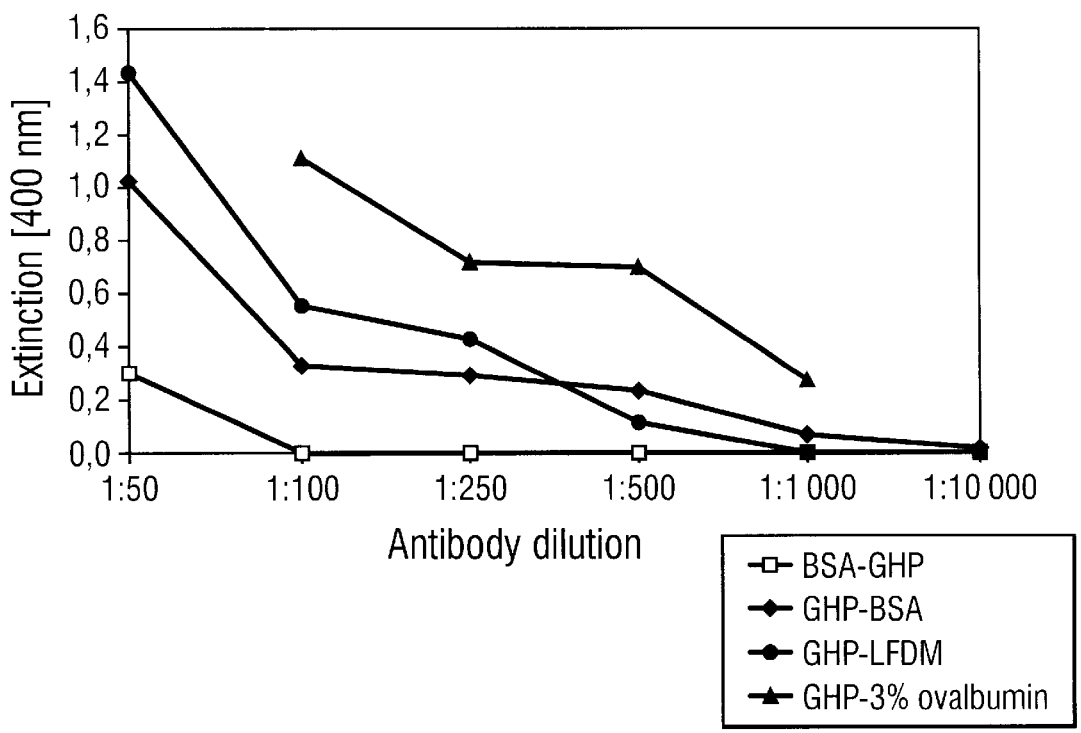
Fig. 1: ELISA Enzyme Linked Immunosorbent Assay
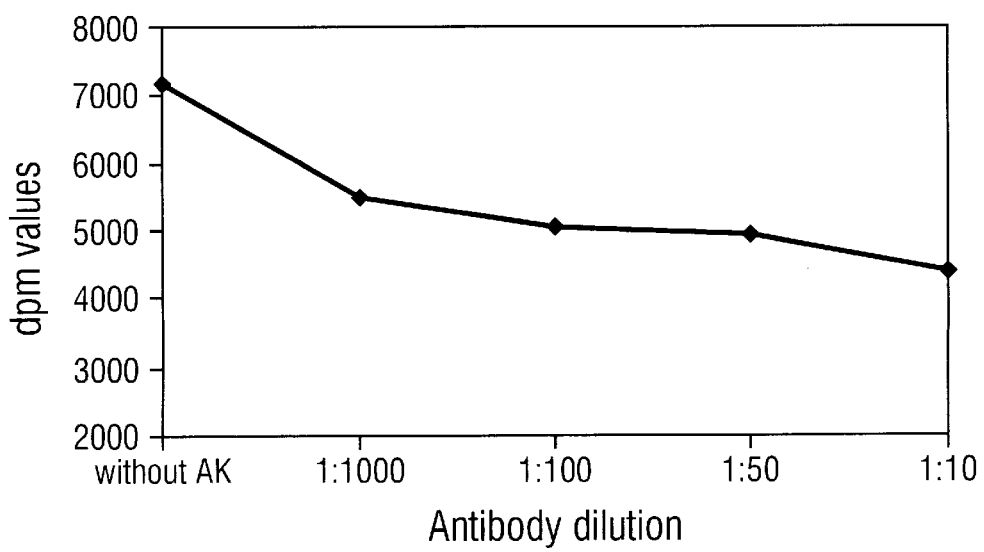
Fig. 2: DPM in the incubation supernatant

ANTIBODIES FOR THE SELECTIVE IMMUNOLOGICAL DETERMINATION OF BILE ACIDS IN BIOLOGICAL MATRICES

Description

Antibodies for the selective immunological determination of bile acids in biological matrices The present invention relates to polyclonal antibodies for the selective immunological determination of bile acids in biological matrices, a process for the production of these antibodies, and their use in immunoassays.

Bile acids form the final product of cholesterol metabolism and their determination has great diagnostic importance with respect to the recognition and treatment of metabolic disorders, liver disorders and gastrointestinal malfunctions (K. D. R. Setchell and A. Matsui, Clin. Chim. Acta 127, 1983, pp. 1–17 ).

The processes currently available for the exact determination of bile acids in biological matrices, such as, for example, serum, feces, urine and tissue samples, have the disadvantage of either being very labor-intensive for clinical practice, or of being of not very selective or too insensitive. Immunoassays, however, have the crucial advantage of not only being extremely selective, but also of allowing highly sensitive determinations.

On the basis of the specific properties of the analyte, the immunoassays for bile acids to date were all designed as competitive radioimmunoassays, as the type of immunization (use of bile acids coupled to bovine serum albumin) only resulted in not very specific and poorly binding antibodies (A. Roda et al., Talanta 31, pp. 895–900, 1984).

In contrast, it is the object of the present invention to make available polyclonal antibodies which have good binding properties and a high specificity to bile acids and a process for their production.

The present invention is further based on the object of making available a process for the immunological determination of bile acids based on the antibodies to be developed, in which a rapid and accurate determination of the bile acid contents in biological matrices is guaranteed.

The object is achieved according to the invention by a polyclonal antibody 1. with specificity for bile acid homopolymers,
2. and with specificity for the respective repetitive subunits.

The object set is moreover achieved by a process for the immunological determination of bile acids using an antibody and a labeled second antibody which binds to the first antibody, wherein the first antibody is a polyclonal antibody according to the present invention. The invention is explained in detail in the following. The invention is furthermore defined by the patent claims.

By means of immunization of a suitable vertebrate species, such as, for example, rabbit, sheep, pig, goat, chicken, etc. with a specific homopolymer, it has now been succeeded in generating antibodies not only against the antigen itself, but also against the repetitive subunits. This process is a completely novel way of generating antibodies against low-molecular weight units.

In the case of this specific homopolymer, we are dealing with polymeric or oligomeric bile acids which can be prepared by polymerization of monomeric bile acids of the formula I $$G—X—A \qquad (I)$$

in which

G is a bile acid radical or derivative,

X is a bridge group and

A is a polymerizable, ethylenically unsaturated group.

BRIEF DESCRIPTION OF THE DRAWINGS

FIG. 1 shows an ELISA assay for antibodies against the cholic acid homopolymer.

FIG. 2 shows the determination of bile acids using the antiserum against bile acid homopolymers.

Among the compounds of the formula I, the following are preferred:

Compounds in which

G is a free bile acid or its alkali metal or alkaline earth metal salt or a bile acid esterified on ring D, which is bonded via its ring A or B, preferably via ring A, to the group X for which preferably the formula II applies $$(Y)_o—(Z)_p \qquad (II),$$

in which

Y is adjacent to G and is —O—, —NR—, —O—(C=O)—, —NR—(C=O)—,

Z is $(C_1-C_{12})$-alkylene or $(C_7-C_{13})$-aralkylene, it being possible to replace individual, preferably 1 to 4, methylene groups in the alkylene chain of the alkylene or aralkylene radical by groups such as —O—, —NR'—, —NR'—(C=O)—, —O—(C=O)— or —NR'—(C=O)—NR"—, preferably a group of one type, o and p independently of one another are zero or 1, o and p not simultaneously being zero, A is an ethylenically unsaturated group of the formula

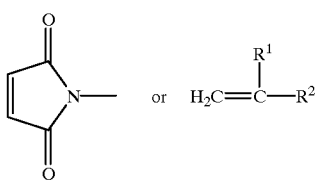

$R^1$ is hydrogen or $CH_3$ and $R^2$ is —NR'—(C=O)—, —O—(C=O)—, —O—, —NR'— or a single bond, the carbonyl groups being adjacent to the C—C double bond, R' is hydrogen or $(C_1-C_6)$-alkylene, preferably $(C_1-C_3)$-alkylene.

Among these, the polymers and oligomers are preferred in which G corresponds to the formula III

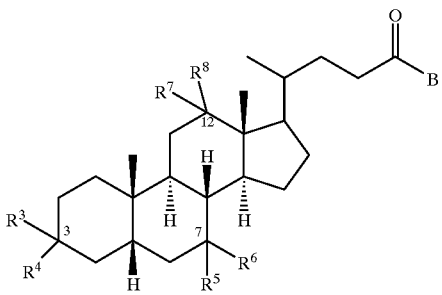

(III)

in which
R$^3$ to R$^8$ independently of one another are hydrogen, OH, NH$_2$ or an OH group protected by an OH protective group and one of the radicals R$^3$ to R$^6$ is a bond to the group X, this bond starting from the positions 3 (R$^3$ or R$^4$) or 7 (R$^5$ or R$^6$), the β-position being preferred, and the other position 7 or 3 in each case carrying an OH group or a protected OH group, B is —OH, —O-alkali metal, —O-alkaline earth metal, —O—(C$_1$–C$_{12}$)-alkyl, —O-allyl or —O-benzyl, preferably —OH, —O-alkali metal, —O—(C$_1$–C$_6$)-alkyl, —O-allyl or —O-benzyl, alkyl being either n-alkyl or isoalkyl and the ester group formed

being esters which can be hydrolyzed both by acid and by base,

Y is —O—, —NR'—, —O—(C=O)—, —NR'—(C=O)—,

Z is (C$_1$–C$_{12}$)-alkylene, (C$_7$–C$_{13}$)-aralkylene, it being possible for 1 to 3 methylene groups in the alkylene chain to be replaced by the groups —O—, —NR'—, —NR'—(C=O)—, —O—(C=O)—, —NR'—(C=O)—NR"— and o and p independently of one another are zero or 1, o and p not simultaneously being zero, A is

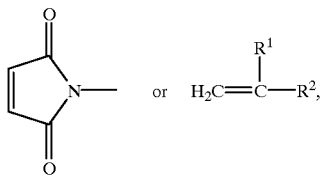

where
R$^1$ is hydrogen or CH$_3$ and
R$^2$ is —NR'—(C=O)—, —NR'— or a single bond, in which
R' is hydrogen or (C$_1$–C$_6$)-alkylene.

If p=zero and o=1, Y is preferably —O—(C=O)— or —NR'—(C=O)—.

If p=1 and o=zero, Z is preferably (C$_1$–C$_{12}$)-alkylene, 1–3 methylene groups, preferably one methylene group, being replaced by —NR'—(C=O)—NR". R' and R" independently of one another are hydrogen or (C$_1$–C$_6$)-alkylene.

If p=1 and o=1, Y is preferably —O—. Among these, it is preferred that Z is (C$_1$–C$_{12}$)-alkylene or (C$_7$–C$_{13}$)-aralkylene, 1 or 2 methylene groups, preferably one methylene group, being replaced by —NR'—(C=O)— or —NR'—(C=O)—NR"—. R' and R" independently of one another are hydrogen or (C$_1$–C$_6$)-alkylene.

Furthermore, amongst these it is preferred that a methylene group of Z is then —NR'—(C=O)—NR"— if Z itself is an aralkyl radical in which the aryl radical is linked in the meta-position, Z on the one hand as radical A carries a group

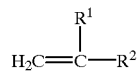

in which R$^2$ is a single bond and on the other hand carries a —NR'—(C=O)—NR"— group which is linked in the meta-position via a methylene group to the aralkylene radical. R' and R" independently of one another are hydrogen or (C$_1$–C$_6$)-alkylene.

Likewise, amongst these it is preferred that if Z is a (C$_1$–C$_{12}$)-alkylene group, at most one methylene group is replaced by —NR'—(C=O)— and the radical A is

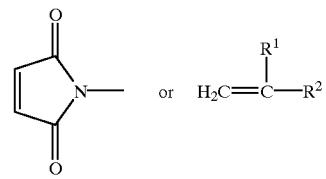

where R$^2$ is —NR'—(C=O)—.

It is furthermore particularly preferred that Y is not directly adjacent to the group replacing a methylene group of Z and also is not adjacent to

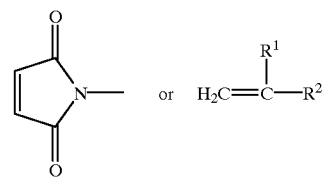

if R$^2$ is a single bond.

Among the OH protective groups the following are understood an alkyl radical having 1–10 carbon atoms or an alkenyl radical having 2–10 carbon atoms, the radicals being branched or unbranched, a cycloalkyl radical having 3–8 carbon atoms, a phenyl radical which is unsubstituted or substituted 1–3 times by F, Cl, Br, (C$_1$–C$_4$)—Alkyl or (C$_1$—C$_4$)-alkoxy, a benzyl radical which is unsubstituted or substituted 1–3 times by F, Cl, Br, (C$_1$–C$_4$)—alkyl or (C$_1$–C$_4$)-alkoxy or an R'"-(C=O)— radical, where R'" is hydrogen or (C$_1$–C$_4$)-alkyl.

Very particularly preferred are 2-homopolymers which were prepared as described below.

In the following examples, bile acid methyl esters of the formula VI are used.

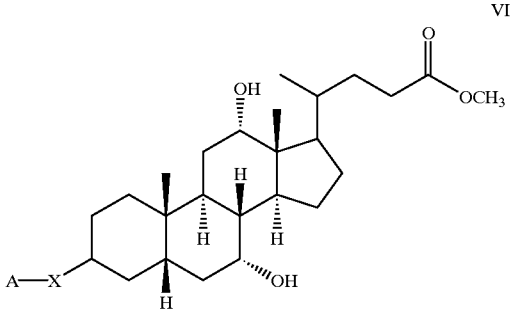

VI

The group A-X is in each case defined in the examples.

For dialysis, dialysis tubing from the company Spectrum Medical Industries, INC. with the name Spectra/Por No. 3 having an exclusion limit of 3500 g/mol was employed.

The determination of the weight-average molecular weights was carried out by means of GPC in comparison with polystyrene standards.

Chromatograph: ALC/GPC 244 Waters Chromatography

Column set: 4 Ultrastyragel columns

Solvent: THF

Flow rate: 1 ml/min

Sample amount: 0.4 ml of sample solution of c=0.2 g/dl

Detector: RI+4X

COMPOUND 1

1110 mg of a bile acid methyl ester, where A—X=$H_2C$=CH—(C=O)—NH—$(CH_2)_6$—O—, are dissolved in 8 ml of tetrahydrofuran under nitrogen in a reaction vessel and treated with 150 mg of 75% strength dibenzoyl peroxide, dissolved in 0.75 ml of toluene. The reaction mixture is heated at 75° C. or 18 hours with stirring. The reaction mixture is then diluted with 10 ml of THF and treated with 0.5 ml of 20% strength aqueous sodium hydroxide solution. After about 10 minutes, the turbidity of the reaction mixture which occurs is dissolved by addition of water. This process is repeated until turbidity of the mixture no longer occurs. The reaction mixture is then diluted with 30 ml of water, dialyzed for 24 hours against deionized water (cut-off: 3500 g/mol) and freeze-dried.

Weight average molecular weight of the unhydrolyzed substance:

$M_w$=10,000 g/mol (determined by GPC).

COMPOUND 2

386.8 mg of a bile acid methyl ester, where A—X=$H_2C$=CH—(C=O)—NH—$(CH_2)_2$—O—, are dissolved in 2.78 ml of tetrahydrofuran in a reaction vessel under nitrogen and treated with 52 mg of 75% strength dibenzoyl peroxide, dissolved in 0.5 ml of toluene. The reaction mixture is heated at 75° C. for 18 hours with stirring. The reaction mixture is then diluted with 10 ml of THF and treated with 0.5 ml of 20% strength aqueous sodium hydroxide solution. After about 10 minutes, the turbidity of the reaction mixture which occurs is dissolved by addition of water. This process is repeated until turbidity of the mixture no longer occurs. The reaction mixture is then diluted with 30 ml of water, dialyzed for 24 hours against deionized water (cut-off: 3500 g/mol) and freeze-dried.

Weight-average molecular weight of the unhydrolyzed substance:

$M_w$=11,000 g/mol (determined by GPC).

1. Production of the antibodies

The appropriate homopolymer was first homogenized with 3 mg of incomplete Freund's adjuvant and then used for the immunization. Administration was carried out 8 times in a period of 16 weeks. The amount injected in each case was in the range from 0.001 g–10 mg of the homopolymer in each case, suspended in incomplete Freund's adjuvant, and was preferably administered intramuscularly to a suitable vertebrate, e.g. rabbit, pig, sheep, goat, chicken, etc. 10 days after the respective injection, a serum sample was obtained and examined for the presence of the antibodies according to the invention using a suitable test process, e.g. using the dot-blot process, using ELISA methodology or with the aid of an RIA process (see also Section 2). In the case of chickens, it is possible 10 days after the injection to collect the eggs and to obtain the antibodies from them using the EGGstract® chicken IgY purification system of the company Promega.

2. Detection of antibodies against the cholic acid homopolymer in the serum of a donor animal in the dot-blot process Various commercially available bile acids (Sigma) or the bile acid homopolymer are dissolved at a concentration of 1 mg/ml in IEF buffer (0.25 M tris base, 2 M glycine, 0.02% sodium dodecylsulfate, 0.25% Nonidet® NP40 (Sigma), 25 mg/25 ml dithiothreitol, 37 mg/25 ml EDTA). These stock solutions are employed in various dilutions (1:10–1:10,000) and 10 µl each are applied to an Immobilon® membrane (Millipore) activated with methanol/water. The membrane is then dried at 60° C. in a drying cabinet in order to immobilize the antigens on the membrane. The membrane is in turn activated by laying it, with the side not coated with antigen, on methanol/water. The blocking of uncoated membrane areas to avoid nonspecific antibody binding is carried out by incubating the membrane at 4° C. with 5% low-fat dry milk (LFDM) in TBS (tris-buffered saline) overnight. It is then washed for 3×10 min with 0.1% LFDM/TBS and the membrane is incubated for 120 min with the antiserum solution diluted in TBS (dilutions up to 1:1000). It is again washed for 3×10 min and incubated in a manner known from the literature with a suitable second antibody which can be, for example, radio-fluorescence specific, chemiluminesence-or enzyme-labeled. If the first antibody, which was generated against a specific antigen, originates from the sheep, an anti-sheep peroxidase antibody (dilution 1:1000 in 0.1% LFDM/TBS), for example, is taken to detect whether an antigen-antibody reaction has taken place. Then, for example, 10 mg of diaminobenzidine can be dissolved in 15 ml of 0.1 M tris/HCl buffer pH 7.4 as a color reagent for the peroxidase reaction and the detection reaction can be started by addition of 12 µl of 30% strength $H_2O_2$.

In the case of the determination of a bile acid homopolymer, it was possible to detect the antigen in a concentration-dependent manner at an antiserum dilution of 1:200 up to 1:5000 (use of a 1 mg/ml stock solution). The detection of free bile acids can only be achieved qualitatively at low dilutions, since the different bile acids have different hydrophobicities and as a result the adhesion, for example, of chenodeoxycholic acid to the membrane is not identical to, for example, taurocholic acid, or the many different bile acids now adhere to the Immobilon membrane with differing affinity.

2.1. ELISA (enzyme-linked immunosorbent assay) for the determination of antibodies against the cholic acid homopolymer (FIG. 1)

The antibodies in the whole serum obtained from the immunized animals are purified by ammonium sulfate precipitation. To do this, according to the instructions from "Biochemische Arbeitsmethoden" [Biochemical Working Methods] (in T.G. Cooper, W. de Gruyter Verlag), the serum is adjusted to a 25% strength $(NH_4)_2SO_4$ degree of saturation by very slow stirring at 4° C. with a saturated ammonium sulfate solution. After stirring at 4° C. for 6 hours, the precipitate is removed by centrifugation at 3000×g. The supernatant is then adjusted to a 50% strength $(NH_4)_2SO_4$ degree of saturation with the saturated $(NH_4)_2SO_4$ solution. The mixture is again stirred at 4° C. for 6 hours and the precipitate containing the antibodies is obtained by a 3000×g centrifugation. The precipitate is taken up in TBS and dialyzed at 4° C. for 3×12 h against TBS-0.05% sodium azide pH 7.5.

As bile acids also exhibit high albumin binding, various blocking solutions were tested in parallel in order on the one hand to be able to assess the nonspecific bindings and interferences of the blocking solution.

Solution 1: 0.1 M sodium carbonate pH 9.6
  0.02% sodium azide
Solution 2: 0.015% Tween® 20 (Sigma) in TBS pH 7.4
Solution 3: 50 mM glycine, pH 9.6
  0.5 mM $MgCl_2$
  directly before incubation 1 mg/ml of p-nitrophenyl phosphate is dissolved.

Batch a:

3% BSA (bovine serum albumin) in solution 1 was incubated overnight at 4° C. in 96-hole plastic plates, then washed 3× with solution 2. The cholic acid homopolymer was then incubated at RT for 3 hours in solution 1 at a concentration of 0.1 mg/ml. Before the anti-cholic acid homopolymer antiserum was incubated for 3 hours in solution 1 at various dilutions, it was washed 3 times with solution 2. Nonspecifically bound antiserum was then removed by washing 3 times with solution 2. Detection was carried out using an anti-sheep igG antibody (produced in donkeys or goats) which is coupled to an alkaline peroxidase.

Batch b:

0.1 mg/ml of cholic acid homopolymer in solution 1 was incubated overnight at 4° C. in 96-hole plastic plates, then washed 3× with solution 2. It was subsequently incubated at RT for 3 hours with 3% BSA in solution 1. Before the anti-cholic acid homopolymer antiserum was incubated at various dilutions in solution 1 for 3 hours, it was washed 3 times with solution 2. Nonspecifically bound antiserum was then removed by washing 3 times with solution 2. Detection was carried out using an anti-sheep IgG antibody (produced in donkeys or goats) which is coupled to an alkaline peroxidase.

Batch c:

0.1 mg/mi of cholic acid homopolymer in solution 1 was incubated overnight at 4° C. in 96-hole plastic plates, then it was washed 3× with solution 2. Subsequently, it was incubated at RT for 3 hours with 3% low-fat dry milk in solution 1. Before the anti-cholic acid homopolymer antiserum was incubated at various dilutions in solution 1 for 3 hours, it was washed 3 times with solution 2. Nonspecifically bound antiserum was then removed by washing 3 times with solution 2. Detection was carried out as described in a).

Batch d:

0.1 mg/ml of cholic acid homopolymer in solution 1 was incubated overnight at 4° C. in ELISA plates, then washed 3× with solution 2. It was subsequently incubated at RT for 3 hours with 3% egg albumin (Sigma) in solution 1. Before the anti-cholic acid homopolymer antiserum was incubated at various dilutions in solution 1 for 3 hours, it was washed 3 times with solution 2. Nonspecifically bound antiserum was then removed by washing 3 times with solution 2. Detection was carried out as described in a).

Reaction with the alkaline peroxidase-labeled anti-sheep IgG antibody The commercially available antibody was incubated for 2 hours in solution 1 at a dilution of 1:1000, and after washing 3 times with solution 1 (without sodium azide), the detection reaction was started by addition of solution 3 and the extinction of 400 nm was determined in an ELISA reader after a reaction period of 15 minutes (see FIG. 1).

In FIG. 1, the 0 value subtracted is the corresponding antibody dilution without incubation with the bile acid homopolymer (GHP).

3. Determination of bile acids using the antiserum against bile acid homopolymers (FIG. 2)

1.5 ml of the antiserum according to the invention, e.g. from sheep, is stirred for 15 minutes with 75 mg of active carbon in order to remove bile acids present in the serum. The active carbon is then removed by centrifugation for 20 min at 9000×g and by filtration through a 0.45 μm filter. The serum is furthermore diluted 1:2 with 0.01 M potassium phosphate buffer pH 7.4 (KP buffer).

Antibodies in the antiserum are purified using the protein G kit from Pierce and a dilution series is prepared with KP buffer up to 1:10,000.

100 μl of a $[^{14}C]$-TCA-solution (8000 dpm) is combined with 100 μl of the variously diluted antibody solutions and made up to 1000 μl with KP buffer. The sample is incubated at 42° C. for 60 minutes and then at 4° C. for 45 minutes. 0.5 ml of a 37.5% polyethylene glycol solution in KP is then added and the mixture is incubated for a further 10 minutes. Precipitation at 1200×g is then carried out at 4°. The supernatant is removed and the amount of $[^{14}C]$-TCA not precipitated after antibody binding is counted in a scintillation counter after addition of 10 ml of scintillation fluid (see FIG. 2).

Using the antibody produced, the bile acid homopolymer can be detected and identified in a concentration-dependent manner in an ELISA. The fact that this polyclonal antibody itself can be employed for the detection of highly dilute bile acid samples, as the antigen-antibody reaction also takes place at high dilution, is shown by use of $^{14}$C-TCA. This antibody is thus also suitable for the analysis of serum samples of low bile acid content.

The abbreviations used mean:
IEF=isoelectric focusing
KP=potassium phosphate buffer
TCA=taurocholic acid
EDTA=disodium ethylenedinitrilotetraacetate
GPC=gel permeation chromatography
TBS=tris-buffered saline
LFDM=low-fat dry milk
BSA=bovine serum albumin
RIA=radioimmunoassay
ELISA=enzyme-linked immunosorbent assay

We claim:

1. An antibody which binds to a bile acid, said antibody being prepared by immunizing a vertebrate animal with a homopolymer, wherein said homopolymer is prepared by polymerization of monomeric bile acids of the formula I

G—X—A   (I)

wherein
  G is a bile acid, an alkali metal thereof, alkaline earth metal salt thereof, or an esterified bile acid;
  X is a bridge group; and
  A is a polymerizable, ethylenically unsaturated group.

2. An antibody as claimed in claim 1, wherein
  G is a free bile acid, an alkali metal thereof, alkaline earth metal salt thereof, or a bile acid esterified on ring D, wherein said bile acid is bonded via its ring A to the group X;
  X is a bridge group of the formula II

$(Y)_o$—$(Z)_p$   (II), wherein
  Y is —O—, —NR', —O—(C=O)—, or —NR'—(C=O)—, Y being adjacent to G;

Z is ($C_1$–$C_{12}$)-alkylene or ($C_7$–$C_{13}$)-aralkylene;
o,p independently of one another are zero or 1, o and p not simultaneously being zero; and
A is an ethylenically unsaturated group of the formula

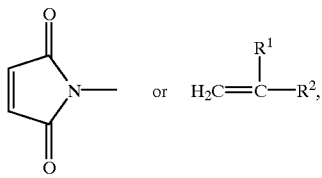

wherein
$R^1$ is hydrogen or $CH_3$, and
$R^2$ is —NR'—(C=O)—, —O—(C=O)—, —O—, —NR'—, or a single bond, the carbonyl groups being adjacent to the C—C double bond; and
R', R" are hydrogen or ($C_1$–$C_6$)-alkylene.

3. An antibody as claimed in claim 1, wherein the homopolymer is prepared under a nitrogen atmosphere by reaction at 75° C. for 18 hours of 1110 mg of the bile acid methyl ester of the formula

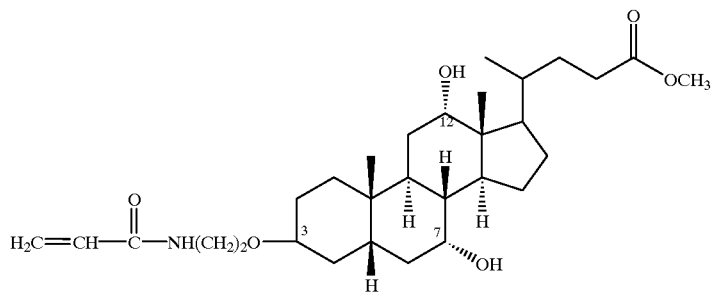

dissolved in 8 ml of tetrahydrofuran, with 150 mg of 75% strength dibenzoyl peroxide, dissolved in 0.75 ml of toluene.

4. An antibody as claimed in claim 1, wherein the homopolymer is prepared under a nitrogen atmosphere by reaction at 75° C. for 18 hours of 386.8 mg of the bile acid methyl ester of the formula

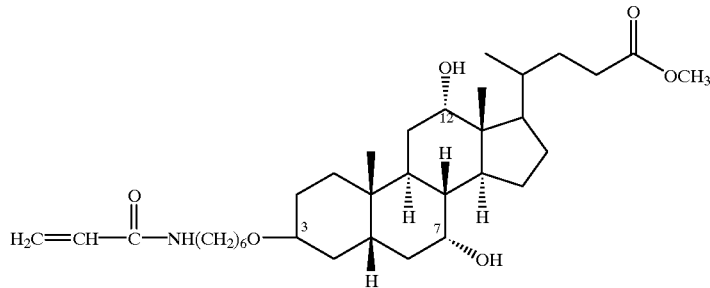

dissolved in 2.78 ml of tetrahydrofuran, with 52 mg of 75% strength dibenzoyl peroxide, dissolved in 0.5 ml of toluene.

5. An immunoassay kit for the determination of bile acids in a biological sample, comprising an antibody as claimed in claim 1.

6. The antibody of claim 2, wherein the individual methylene groups of the alkylene chain of group Z are replaced with —O—, —NR', —NR'—(C=O)—, —O—(C=O)—, or —NR'—(C=O)—NR"—.

7. An antibody as claimed in claim 1, wherein G is

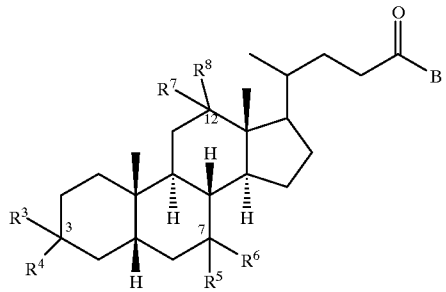

wherein $R^3$ to $R^8$ independently of one another are hydrogen, OH, $NH_2$, or an OH group protected by an OH protective group, wherein one of the radicals $R^3$ or $R^4$ is bonded to group X; and
B is an ester selected from —OH, —O-alkali metal, —O-alkaline earth metal, —O—($C_1$–$C_{12}$)-alkyl, —O-allyl, or —O-benzyl, wherein said alkyl is an n-alkyl or an isoalkyl and wherein said ester can be hydrolyzed by both an acid and a base.

8. The antibody of claim 2, wherein G is

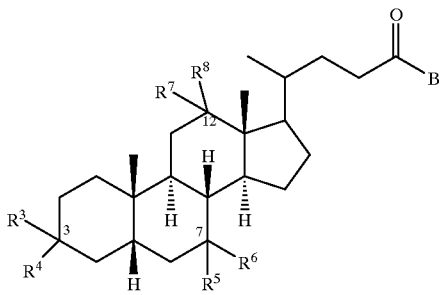

wherein

R³ to R⁸ independently of one another are hydrogen, OH, NH$_2$, or an OH group protected by an OH protective group, in which one of the radicals R³ or R⁴ is bonded to group X; and B is an ester selected from —OH, —O-alkali metal, —O-alkaline earth metal, —O—(C$_1$–C$_{12}$)-alkyl, —O-allyl, or —O-benzyl, wherein said alkyl is an n-alkyl or an isoalkyl, and wherein said ester can be hydrolyzed by both an acid and a base.

9. A process for the production of an antibody which binds to a bile acid, comprising the steps of:

a) preparing a homopolymer by polymerization of monomeric bile acids of the formula I

G—X—A     (I)

wherein

G is a bile acid an alkali metal or alkaline earth metal salt thereof, or an esterified bile acid;

X is a bridge group; and

A is a polymerizable, ethylenically unsaturated group;

b) immunizing a vertebrate animal with said homopolymer; and c) obtaining the antibody produced by said vertebrate.

10. A method of determination of a bile acid in a biological sample comprising the steps of:

a) performing an immunoassay using the antibody of claim 1; and b) determining the amount of said bile acid.

* * * * *